United States Patent [19]

Hubele

[11] 4,025,648
[45] May 24, 1977

[54] HALOACYLANILIDES AND USE AS FUNGICIDES

[75] Inventor: Adolf Hubele, Magden, Switzerland

[73] Assignee: Ciba-Geigy Corporation, Ardsley, N.Y.

[22] Filed: Mar. 27, 1975

[21] Appl. No.: 562,721

[30] Foreign Application Priority Data

Apr. 1, 1974 Switzerland .................. 4509/74
Feb. 13, 1975 Switzerland .................. 1785/75

[52] U.S. Cl. .................. 424/309; 260/471 A
[51] Int. Cl.² .................. C07C 103/46
[58] Field of Search .......... 260/471 A; 424/309; 71/111

[56] References Cited

UNITED STATES PATENTS

| | | | |
|---|---|---|---|
| 3,712,805 | 1/1973 | Yates et al. | 71/111 X |
| 3,763,216 | 10/1973 | Bertrand | 260/471 A |
| 3,780,090 | 12/1973 | Akiba et al. | 260/471 A |
| 3,780,095 | 12/1973 | Klemm et al. | 260/471 A X |
| 3,892,786 | 7/1975 | Baker et al. | 260/468 E |

FOREIGN PATENTS OR APPLICATIONS 730,316  1/1973  South Africa

*Primary Examiner*—Richard L. Raymond
*Attorney, Agent, or Firm*—Harry Falber

[57] ABSTRACT

A microbicidal composition is described which contains as active substance a compound of the formula I

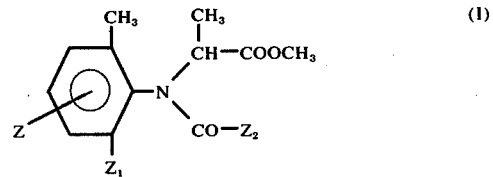

wherein Z represents hydrogen or methyl, $Z_1$ represents methyl or ethyl, $Z_2$ represents an alkyl group of 2 to 4 carbon atoms which is substituted by a chlorine, bromine or iodine atom, together with suitable carriers and optionally other additives which promote the application.

23 Claims, No Drawings

HALOACYLANILIDES AND USE AS FUNGICIDES

The present invention provides compounds of the formula I

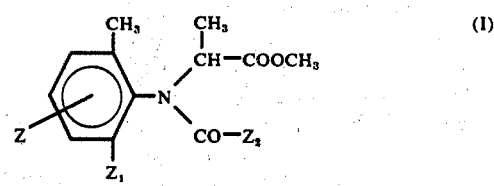

wherein Z represents hydrogen or methyl, $Z_1$ represents methyl or ethyl, $Z_2$ represents an alkyl group of 2 to 4 carbon atoms which is substituted by a chlorine, bromine or iodine atom, a process for the manufacture of these compounds, as well as microbicidal compositions which contain these novel compounds as active substances, and also a method of combating phytopathogenic fungi and bacteria which comprises the use of the compounds of the formula I.

An alkyl group of 2 to 4 carbon atoms is ethyl, n-propyl, isopropyl, n-butyl, isobutyl, sec. butyl.

German Offenlegungsschrift 2,212,268 discloses in general terms that N-haloacylated anilinoalkanecarboxylic esters possess selective herbicidal action. However, only a number of N-haloacylated 2,6-dialkylanilinoacetic acids and esters thereof are mentioned by name and shown to be herbicides. No references as to microbicidal, especially plant fungicidal, action are provided.

The group of N-(1'-methoxycarbonylethyl)-N-haloacyl-2,6-dialkylanilines of the formula I of this invention has so far not been described in the literature and is therefore novel. It is extremely surprising that this group, in contradistinction to the anilinoacetic acids and esters of DOS 2,212,268, possess pronounced plant fungicidal properties.

The compounds with the characteristic chemical structure of the formula I have both preventive and curative action against phytopathogenic fungi on cultivated plants, e.g. cereals, maize, rice, vegetables, sugar beets, soya, ground nuts, fruit trees, ornamental plants, but principally on vines, hops, cucumber plants (cucumber, marrows, melons) and solanaceae, such as potatoes, tobacco and tomatoes, as well as on banana, cocoa and rubber plants.

With the active substances of the formula I it is possible to inhibit or to destroy the fungi which occur on plants or parts of plants (fruit, blossoms, leaves, stems, tubers, roots) and to protect from such fungi the parts of plants which grow later. The active substances act against the phytopathogenic fungi which belong to the following classes: ascomycetes (erysiphaceae); basidiomycetes, above all rust fungi; fungi imperfecti (moniliales); but especially against the oomycetes which belong to th class of the phycomycetes, e.g. phytophthora, peronospora, pseudoperonospora, pythium or plasmopara. In addition, the compounds of the formula I have a systemic action. They can also be used as seed-dressing agents for protecting seeds (fruit, tubers, kernels) and plant cuttings from fungus infections as well as from phytopathogenic fungi which occur in the soil.

In order to broaden or modify the activity spectrum, it is possible to mix the active substances of the formula I with other, known fungicides, bactericides, fungistatic agents, bacteriostaic agents, and also with insecticides, acaricides, herbicides, and, on account of their systemic action, which permits a soil application, also with nematicides, molluscicides or rodenticides, by which means effects which are in part synergistically intensified are obtained.

A preferred group of microbicidal compounds is that of the formula I wherein $Z_1$ represents methyl. This group of compounds will be referred to as sub-group Ia.

A further preferred group of microbicidal compounds is that of the formula I wherein Z represents hydrogen and $Z_1$ represents methyl or ethyl, while $Z_2$ represents a group

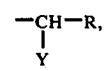

in which R represents methyl or ethyl and Y represents chlorine or bromine. Ib group of compounds will be referred to as sub-group Ib.

The compounds of the formula I possess an asymmetrical carbon atom in the propionic ester side-chain. Compounds of the formula I, Ia and Ibin the D-configuration have the more pronounced microbicidal action and are therefore preferred. Depending on the substitution, a number of the compounds can have a second asymmetrical carbon atom in the haloalkyl side-chain $Z_2$. If no optically active starting materials are used in the manufacture, then a diastereoisomer mixture is inevitably obtained. Unless it is otherwise stated to the contrary in the following portion of the disclosure, an active substance of the formula I is always to be understood as meaning the diastereoisomeric mixture.

The compounds are manufactured, for example, by initially reacting an aniline of the formula II

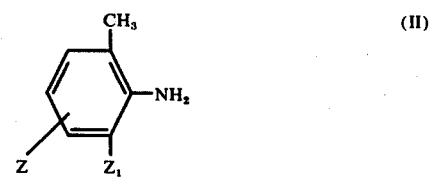

with the desired α-halogenopropionic acid methyl ester of the formula III

and by reacting according to the invention the compound of the formula IV

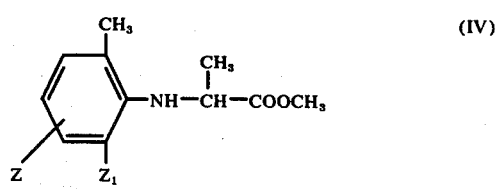

with the desired halogenoalkanecarboxylic acid HOOC-$Z_2$ or the reactive acid halide, acid anhydride, ester or amide thereof, preferably with the halide or anhydride of the appropriate chloro-, bromo- or iodoalkanecarboxylic acid.

In the above formulae, Z, $Z_1$ and $Z_2$ have the meanings assigned to them in formula I and Hal represents halogen, preferably chlorine or bromine. Preferred acid halides are the acid chlorides or acid bromides.

The reactions can be carried out in the presence or absence of solvents or diluents which are inert to the reactants. Examples of solvents or diluents are: aliphatic or aromatic hydrocarbons, e.g. benzene, toluene, xylene, petroleum ether; halogenated hydrocarbons, e.g. chlorobenzene, methylene chloride, ethylene chloride, chloroform; ethers and ethereal compounds, e.g. dialkyl ethers, dioxan, tetrahydrofuran; nitriles, e.g. acetonitrile; N,N-dialkylated amides, e.g. dimethyl formamide; anhydrous acetic acid, dimethyl sulphoxide, ketones, e.g. methyl ethyl ketone, and mixtures of such solvents.

The reaction temperatures are between 0° C and 180° C, preferably between 20° C and 120° C. In many instances, especially when using halogenoacyl halides, the α-haloacylation is carried out in the presence of an acid acceptor or of a condensation agent. Suitable examples are: tertiary amines, such as trialkylamines (e.g. triethylamine), pyridine and pyridine bases, or inorganic bases, for example the oxides and hydroxides, hydrogen carbonates and carbonates of alkali metals and alkaline earth metals as well as sodium acetate. It is furthermore possible to use a surplus of the respective aniline derivative of the formula II as acid acceptor.

The reaction can also be carried out without an acid acceptor. In some instances it is expedient to pass in nitrogen in order to expel the hydrogen halide that has formed. In other cases it may be desirable to carry out the reaction in the presence of dimethyl formamide as catalyst.

Particulars on the manufacture of the intermediates of the formula IV can be inferred from the methods generally indicated for the manufacture of anilinoalkane esters in the following publications: J. Org. Chem. 30, 4101 (1965) Tetrahedron 1967, 487; Tetrahedron 1967, 493.

The pure optical isomers of the formula I are obtained by initially manufacturing the corresponding racemic anilinopropionic acid of the formula V

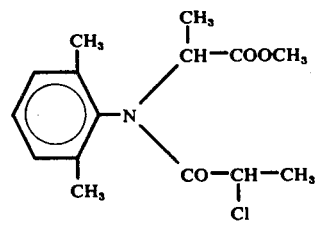

(V)

for example from the aniline of the formula II and the α-halogenopropionic acid, e.g. α-bromopropionic acid, and reacting this compound in known manner with a nitrogen-containing, optically active base. One of the enantiomeric forms of the corresponding compound of the formula V is obtained by fractional crystallisation of the resultant salt and subsequent liberation of the optical D-antipodes, if appropriate also by repeating the reaction with the optically active base. The optically active ester IV can then be formed from this enantiomeric from in conventional manner, for example in the presence of HCl or $H_2SO_4$, with methanol. In analogous manner, the haloalkanecarboxylic acids of the formula HOOC-$Z_2$ — provided they possess an asymmetrical carbon atom — which are necessary for the formation of the anilides of the formula I can be converted with a nitrogen-containing, optically active base into one of the two enantiomeric forms, which in turn can be reacted with an optically active ester of the formula IV. It is thus possible to manufacture the different diastereoisomers of the formula I systematically.

A suitable optically active organic base is, for example, α-phenylethylamine.

Instead of the fractional crystallisation, it is also possible to manufacture the enantiomeric D-forms of the formula IV by diazotising the amino group in the naturally occurring L-aniline in the presence of e.g. HCl or HBr and consequently replacing it by halogen accompanied by the splitting off of $N_2$ and with retention of the L-configuration, subsequently effecting esterification with methanol and then reacting the ester with the aniline of the formula II, when inversion to the D-configurations of the formula IV mostly occurs (J. Am. Soc. 76, 6056).

The following Examples I and II illustrate the manufacture of the active substances of the formula I.

EXAMPLE 1

Manufacture of

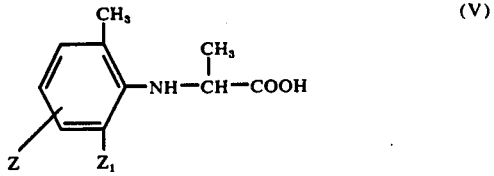

N-(1'-methoxycarbonyl-ethyl)-N-α-chloropropionyl-2,6-dimethylaniline (D,L).

a. Manufacture of the intermediate α-(2,6-dimethylanilino)-propionic acid methyl ester.

67 g of 2,6-dimethylaniline, 125 g of α-bromopropionic acid methyl ester and 53 g of $NaHCO_3$ were stirred for 17 hours at an oil bath temperature of 140° C. After the reaction mixture had cooled, it was diluted with 300 ml of ether. The ethereal extract was washed twice with water, dried over sodium sulphate and filtered. The ether and the excess α-bromopropionic acid methyl ester were distilled off in a water jet vacuum and the crude product was then distilled; b.p. 98° C/0.8 Torr.

b. With stirring, 51.8 g of the propionic ester manufactured according to a) and 35 g of α-chloropropionic chloride were added together to 300 ml of chlorobenzene and the temperature of the reaction mixture rose to 40° C.

After addition of 2 ml of dimethyl formamide, the mixture was refluxed for 2 hours and the chlorobenzene was distilled off in vacuo. The crude product was crystallised by trituration with petroleum ether.

After recrystallisation in toluene, the diastereomeric mixture, which was present in the recrystallised sample in the ratio of c. 2:3 according to the NMR spectrum melted between 108° C and 110° C (compound 1).

EXAMPLE 2

Manufacture of

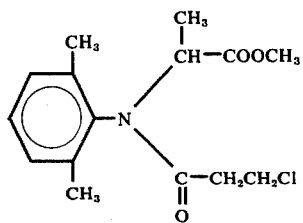

N-(1'-methoxycarbonylethyl)-N-(β-chloroethylcarbonyl)-2,6-dimethylaniline (compound 13).

57 g of 3-chloropropionic chloride in 200 ml of chlorobenzene were added to 74 g of N-(1'-methoxycarbonylethyl)-2,6-dimethylaniline in 300 ml of chlorobenzene. After the weakly exothermic reaction had subsided, 2 ml of dimethyl formamide were added and the mixture was refluxed for 4 hours. After the reaction mixture had cooled, it was washed twice with dilute sodium carbonate solution and twice with water, dried over sodium sulphate and filtered. The solvent was distilled off by rotary evaporation. After recrystallisation from petroleum ether the compound had a melting point of 69°–71° C. The following propionic acid methylesters were also manufactured as intermediates in a manner analogous to that of Example 1a)

α-(2-ethyl-6-methylanilino)-propionic acid methyl ester: b.p. 88°–90° C/0.01 Torr α-(2-ethyl-3,6-dimethylanilino)-propionic acid methyl ester: b.p. 96°–99° C/0.03 Torr α-(2,3,6-trimethylanilino)-propionic acid methyl ester: b.p. 83°–85° C/0.03 Torr; 144°–146° C/9 Torr α-(2,4,6-trimethylanilino)-propionic acid methyl ester; b.p. 88°–90° C/0.04 Torr α-(2-ethyl-5,6-dimethylanilino)-propionic acid methyl ester; b.p. 87°–90° C/0.04 Torr The following compounds of the formula I are manufactured in this manner or by one of the methods indicated hereinbefore, whereby it is possible to manufacture the iodine-containing compounds which are particularly suitable soil fungicides and/or seed dressings for example from the chlorine-containing compounds by halogen substitution with alkali iodide: ($Z_1$= 6-position)

| Compound | Z | $Z_1$ | $Z_2$ | Physical constant |
|---|---|---|---|---|
| 1 | H | $CH_3$ | —CH(Cl)—$CH_3$ | m.p.108°–110° C |
| 2 | H | $CH_3$ | —CH(Br)—$CH_3$ | b.p.148°–152° C/0.05 Torr |
| 3 | H | $CH_3$ | —CH(Cl)—$CH_2$—$CH_3$ | b.p.143°–145° C/0.1 Torr |
| 4 | H | $CH_3$ | —CH(Br)—$CH_2$—$CH_3$ | b.p.140°–142° C/144 0.1 Torr |
| 5 | H | $C_2H_5$ | —CH(Cl)—$CH_3$ | b.p.127°–130° C/0.03 Torr |
| 6 | H | $C_2H_5$ | —CH(Br)—$CH_3$ | b.p.149°–155° C/0.07 Torr |
| 7 | H | $C_2H_5$ | —CH(Cl)—$CH_2$—$CH_3$ | b.p.140°–142° C/0.1 Torr |
| 8 | H | $C_2H_5$ | —CH(Br)—$CH_2$—$CH_3$ | b.p.147°–149° C/0.1 Torr |
| 9 | H | $CH_3$ | —$CH_2$—$CH_2$—$CH_2$—Cl | b.p. 150°–152° C/0.03 Torr |
| 10 | 3-$CH_3$ | $CH_3$ | —$CH_2$—$CH_2$—$CH_2$—Cl | b.p. 158°–162° C/0.03 Torr |
| 11 | H | $C_2H_5$ | —$CH_2$—$CH_2$—$CH_2$—Cl | viscous |
| 12 | 3-$CH_3$ | $C_2H_5$ | —$CH_2$—$CH_2$—$CH_2$—Cl | viscous |
| 13 | H | $CH_3$ | —$CH_2$—$CH_2$—Cl | m.p.69°–71° C |
| 14 | 3-$CH_3$ | $CH_3$ | —$CH_2$—$CH_2$—Cl | m.p.85°–89° C |
| 15 | H | $C_2H_5$ | —$CH_2$—$CH_2$—Cl | semicrystalline |
| 16 | 3-$CH_3$ | $C_2H_5$ | —$CH_2$—$CH_2$—Cl | viscous |
| 17 | 4-$CH_3$ | $CH_3$ | —$CH_2$—$CH_2$—Cl | m.p.99°–100° C |
| 18 | H | $CH_3$ | —$CH_2$—$CH_2$—Br | viscous |
| 19 | 3-$CH_3$ | $CH_3$ | —$CH_2$—$CH_2$—Br | viscous |
| 20 | H | $CH_3$ | —CH(I)—$CH_3$ | b.p.156°–159° C/0.02 Torr |
| 21 | 3-$CH_3$ | $CH_3$ | —CH(I)—$CH_3$ | b.p.162°–164° C/0.01 Torr |
| 22 | 4-$CH_3$ | $CH_3$ | —CH(I)—$CH_3$ | b.p.171°–175° C/0.02 Torr |
| 23 | H | $CH_3$ | —CH(I)—$CH_2$—$CH_3$ | viscous |
| 24 | 3-$CH_3$ | $CH_3$ | —CH(I)—$CH_2$—$CH_3$ | semicrystalline |

-continued

| Compound | Z | $Z_1$ | $Z_2$ | Physical constant |
|---|---|---|---|---|
| 25 | H | $CH_3$ | $-\underset{\underset{Cl}{\mid}}{CH}-CH(CH_3)_2$ | oil, $n_D^{20} = 1.5275$ |
| 26 | 3-$CH_3$ | $CH_3$ | $-\underset{\underset{Cl}{\mid}}{CH}-CH(CH_3)_2$ | viscous |
| 27 | H | $C_2H_5$ | $-\underset{\underset{Cl}{\mid}}{CH}-CH(CH_3)_2$ | viscous |
| 28 | 3-$CH_3$ | $C_2H_5$ | $-\underset{\underset{Cl}{\mid}}{CH}-CH(CH_3)_2$ | semicrystalline |
| 29 | 4-$CH_3$ | $CH_3$ | $-\underset{\underset{Cl}{\mid}}{CH}-CH(CH_3)_2$ | b.p.172°–174° C/ 0.08 Torr |
| 30 | 4-$CH_3$ | $C_2H_5$ | $-\underset{\underset{Cl}{\mid}}{CH}-CH(CH_3)_2$ | b.p.152°–154° C/ 0.04 Torr |
| 31 | H | $CH_3$ | $-CH_2-\underset{\underset{Cl}{\mid}}{CH}-CH_2-CH_3$ | semicrystalline |
| 32 | 3-$CH_3$ | $CH_3$ | $-CH_2-\underset{\underset{Cl}{\mid}}{CH}-CH_2-CH_3$ | b.p.161°–163° C/ 0.02 Torr |
| 33 | H | $C_2H_5$ | $-CH_2-\underset{\underset{Cl}{\mid}}{CH}-CH_2-CH_3$ | viscous |
| 34 | H | $CH_3$ | $-\underset{\underset{Cl}{\mid}}{C}\underset{CH_3}{\overset{CH_3}{<}}$ | m.p.67°–69° C |
| 35 | 4-$CH_3$ | $CH_3$ | $-\underset{\underset{Cl}{\mid}}{CH}CH_3$ | m.p.120° C–122° C |
| 36 | 4-$CH_3$ | $CH_3$ | $-CH_2CH_2CH_2Cl$ | b.p.158°–164° C/ 0.03 Torr |
| 37 | 3-$CH_3$ | $C_2H_5$ | $-\underset{\underset{Cl}{\mid}}{CH}CH_3$ | b.p.137°–139° C/ 0.04 Torr |
| 38 | 3-$CH_3$ | $C_2H_5$ | $-\underset{\underset{I}{\mid}}{CH}CH_3$ | viscous |
| 39 | 5-$CH_3$ | $C_2H_5$ | $-\underset{\underset{Cl}{\mid}}{CH}CH_3$ | viscous |
| 40 | 5-$CH_3$ | $C_2H_5$ | $-\underset{\underset{I}{\mid}}{CH}CH_3$ | b.p.155°–157° C/ 0.03 Torr |

The compounds of the formula I can be used with other suitable pesticides or active substances that promote plant growth in order to widen their activity spectrum.

The compounds of the formula I can be used by themselves or together with suitable carriers and/or other additives. Suitable carriers and additives can be solid or liquid and correspond to the customary substances used in formulation technology, for example natural or regenerated mineral substances, solvents, dispersants, wetting agents, stickers, thickeners, binders or fertilisers. The amount of active substance in commercially useful compositions is between 0.1 and 90%.

The compounds of the formula I can be applied in the following process forms (the percentages by weight in brackets denote the advantageous amounts of active substance): solid forms: dusts and tracking agents (up to 10%); granules, coated granules, impregnated granules and homogeneous granules (1 to 80%); liquid forms:

a. active substance concentrates which are dispersible in water: wettable powders and pastes (25–90% in the commercial pack, 0.01 to 15% in ready for use solution); emulsion concentrates and concentrated solutions (10 to 50%; 0.01 to 15% in ready for use solution);

b. solutions (0.1 to 20%).

The active substances of the formula I can be formulated, for example, as follows:

Dusts: The following substances are used to manufacture a. 50% amd b) a 2% dust:

a. 5 parts of active substance, 95 parts of talcum;

b. 2 parts of active substance, 1 part of highly disperse silicic acid, 97 parts of talcum.

The active substances are mixed with the carriers and ground and in this form can be processed to dusts for application.

Granules: The following substances are used to manufacture 5% granules:

5 parts of active substance
0.25 part of epichlorohydrin
0.25 part of cetyl polyglycol ether
3.50 parts of polyethylene glycol
9 parts of kaolin (particle size 0.3 – 0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such microgranules are advantageously used for combating soil fungi.

Wettable powders: The following constituents are used to manufacture (a) a 70%, (b) a 40%, (c) and (d) a 25% and (e) a 10% wettable powder:

a. 70 parts of active substance, 5 parts of sodium dibutyl naphthylsulphonate, 3 parts of naphthalenesulphonic acid/phenolsulphonic acid/formaldehyde condensate (3:2:1), 10 parts of kaolin, 12 parts of Champagne chalk.

b. 40 parts of active substance, 5 parts of sodium lignin sulphonate, 1 part of sodium dibutylnaphthalenesulphonic acid, 54 parts of silicic acid.

c. 25 parts of active substance, 4.5 parts of calcium lignin sulphonate, 1.9 parts of a Champagne chalk/hydroxyethyl cellulose mixture (1:1), 1.5 parts of sodium dibutylnaphthalenesulphonate, 19.5 parts of silicic acid, 19.5 parts of Champagne chalk, 28.1 parts of kaolin.

d. 25 parts of active substance, 2.5 parts of isooctylphenoxy-polyethylene-ethanol, 1.7 parts of a Champagne chalk/hydroxyethyl cellulose mixture (1:1), 8.3 parts of sodium aluminium silicate, 16.3 parts of kieselguhr, 46 parts of kaolin.

e. 10 parts of active substance, 3 parts of a mixture of the sodium salts of saturated fatty alcohol sulphates, 5 parts of naphthalenesulphonic acid/formaldehyde condensate, 82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of every desired concentration and can be used in particular for application to leaves.

Emulsifiable concentrates: The following substances are used to manufacture a 25% emulsifiable concentrate:

25 parts of active substance
2.5 parts of epoxidised vegetable oil
10 parts of an alkylarylsulphonate/fatty alccohol polyglycol ether mixture
5 parts of dimethyl formamide
57.5 parts of xylene.

By diluting such concentrates with water it is possible to manufacture emulsions of every desired concentration which are especially suitable for application to leaves.

EXAMPLE 3

Action against Phytophthora infestans on Solanum lycopersicum (tomatoes)

Ia. Residual preventive action

Solanum lycopersicum plants of the "Roter Gnom" variety are infected when 3 weeks old with a zoospore suspension of Phytophthora infestans after they have been sprayed with a broth prepared from the active substance processed to a wettable powder and containing 0.05% of active substance, and dried. They are then kept for 6 days in a climatic chamber at 18° to 20° and high humidity, which is produced with an artificial wet fog. After this time typical leaf specks appear. Their number and size are the criterion for evaluating the tested substance.

*Ib*. Curative action:

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the surface of the plants has been dried, they are sprayed with a broth which contains the active substance formulated as wettable powder in a concentration of 0.05%. After the spray coating has dried, the plants are again kept in the humid chamber for 4 days. Size and number of the typical leaf specks which have occured during this time are the criterion for evaluating the effectiveness of the tested substances.

II. Preventive-systemic action

The active substance is applied as wettable powder in a concentration of 0.05% (referred to the volume of the soil) to the surface of the soil of 3 week old "Roter Gnom" tomatoes in pots. Three days later the underside of the leaves of the plants are sprayed with a zoospore suspension of Phytophthora infestans. The plants are then kept for 5 days in a spray chamber at 18° to 20° C and saturated humidity, after which time typical leaf specks form. The size and number of the specks serve as criterion for evaluating the effectiveness of the tested substances. In these three tests, the compounds of the formula I effect the pronounced leaf-fungicidal action illustrated in the Table.

Table

| | (averge values) | | |
|---|---|---|---|
| Compound | Fungus infection in % | Compound | Fungus infection in % |
| 1 | 0–5 % | 25 | < 20 % |
| 2 | < 20 % | 26 | < 20 % |
| 3 | 0–5 % | 27 | < 20 % |
| 4 | < 20 % | 28 | < 20 % |
| 5 | < 20 % | 29 | < 20 % |
| 7 | 20–40 % | 30 | 20–40 % |
| 9 | < 20 % | 31 | < 20 % |
| 11 | < 20 % | 32 | < 20 % |
| 12 | < 20 % | 34 | 0–5 % |
| 13 | < 20 % | 35 | 0–5 % |
| 14 | < 20 % | 36 | < 20 % |
| 15 | < 20 % | 37 | < 20 % |
| 17 | < 20 % | 39 | < 20 % |
| 19 | < 20 % | | |

Compound No. 1 reduces the fungus infection to <20% in the same tests at application concentrations of only 0.02%.

EXAMPLE 4

Action against Plasmopara viticola (Bert. et Curt.) (Berl. et De Toni) on vines a. Residual preventive action Vine cuttings of the variety "Chasselas" were reared in a greenhouse. Three plants in the 10 leaf stage were sprayed with a broth prepared from the active substance and formulated as a wettable powder. After the coating layer had dried, the plants were infected on the underside of the leaves with the spore suspension of the fungus. The plants were subsequently kept for 8 days in a humid chamber, after which time symptoms of the disease were visible on the control plants. The number and size of the infected areas on the treated plants served as criterion for evaluating the effectiveness of the tested active substances.

b. Curative action

Vine cuttings of the variety "Chasselas" were reared in a greenhouse and infected in the 10 leaf stage with a spore suspension of Plasmopara viticola on the underside of the leaves. After they had been kept for 24 hours in a humid chamber, the plants were sprayed with an active substance broth prepared from a wettable powder of the active substance. The plants were then kept for a further 7 days in a humid chamber, after which time the symptoms of the disease were visible on the control plants. The size and number of the infected areas served as criterion for evaluating the effectiveness of the tested substances.

In both these tests of Example 4 the compounds of the formula I effect a pronounced fungicidal action in the following concentrations:

Table

| Compound | Fungus infection in % (average values) | Compound | Fungus infection in % |
|---|---|---|---|
| 1 | 0–5 % | 17 | < 20 % |
| 2 | < 20 % | 18 | < 20 % |
| 3 | 0–5 % | 19 | < 20 % |
| 4 | < 20 % | 20 | < 20 % |
| 5 | < 20 % | 21 | < 20 % |
| 6 | < 20 % | 22 | < 20 % |
| 8 | 20–40 % | 25 | 20–40 % |
| 9 | 0–5 % | 26 | 20–40 % |
| 10 | 0–5 % | 27 | < 20 % |
| 11 | 0–5 % | 28 | 20–40 % |
| 12 | 0–5 % | 29 | < 20 % |
| 13 | 0–5 % | 30 | 20–40 % |
| 14 | 0–5 % | 31 | 20–40 % |
| 15 | < 20 % | 32 | 20–40 % |
| 16 | < 20 % | 33 | 20–40 % |
| 34 | 0–5 % | 37 | < 20 % |
| 35 | 0–20 % | 38 | < 20 % |
| 36 | 0–5 % | 39 | < 20 % |

In application concentrations of only 0.02%, compounds 1, 3, 9, 10, 13, 14 and 34 reduce the fungus infection to <20% in the same tests. The D-forms of compounds 1, 3, 9, 13 and 34 derived from the D-configuration of N-(1'-methoxycarbonylethyl)-2,6-dimethylaniline reduce the fungus infection to 0–10% at rates of application of 0.02%.

EXAMPLE 5

Action against Pythium debaryanum in Beta vulgaris (sugar beet)

a. Action after soil application

The fungus is cultivated on sterile oat kernels and added to a mixtutre of earth and sand. Flower pots are filled with the infected soil in which sugar beet seeds are then sown. Immediately after sowing, the test preparations formulated as wettable powders are poured in the form of aqueous suspensions over the soil (0.002% active substance referred to the volume of the soil). The pots are then stood for 2–3 weeks in a greenhouse at 20°–24° C. The soil is kept uniformly moist by gently spraying it with water. The emergence of the sugar beet plants as well as the number of healthy and sick plants are ascertained in evaluating the tests.

b. Action after seed dressing application

The fungus is cultivated on sterile oat kernels and added to a mixture of earth and sand. Flower pots are filled with the infected soil and sugar beet seeds which have been treated with the test preparations formulated as seed dressing powders are sown therein (0.1% active substance referred to the weight of the seeds). The pots are then stood in a greenhouse for 2–3 weeks at 20°–24° C. The soil is kept uniformly moist by gently spraying it with water. The emergence of the sugar beet plants as well as the number of healthy and sick plants are ascertained.

Under the conditions of both test a) and test b), 80% of the sugar beet plants emerged after treatment with one of the active substances of the formula I and had a healthy appearance. On treatment with one of the iodine-containing active substances 20, 21, 22, 23, 24, 38 and 40, 90% and more of the sugar beet plants emerged healthy. Less than 20% of the control plants emerged and had in part a sickly appearance.

I claim:

1. A haloacylanilide of the formula I

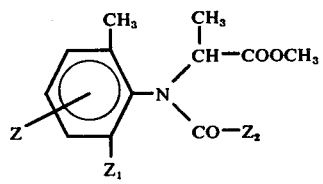

wherein Z represents hydrogen or methyl, $Z_1$ represents methyl or ethyl and $Z_2$ represents an alkyl group of 2 to 4 carbon atoms which is substituted by a chlorine, bromine or iodine atom.

2. The compound of the formula I according to claim 1, wherein $Z_1$ represents methyl.

3. The compound of the formula I according to claim 1, wherein Z represents hydrogen, and $Z_1$ represents methyl or ethyl, and $Z_2$ represents a group

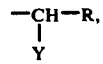

in which R represents methyl or ethyl and Y represents chlorine or bromine.

4. N-(1'-methoxycarbonyl-ethyl)-N-α-chloropropionyl-2,6-dimethylaniline according to claim 1.

5. N-(1'-methoxycarbonyl-ethyl)-N-α-chlorobutyryl-2,6-dimethylaniline according to claim 1.

6. N-(1'-methoxycarbonyl-ethyl)-N-δ-chlorobutyryl-2,6-dimethylaniline according to claim 1.

7. N-(1'-methoxycarbonyl-ethyl)-N-β-chloropropionyl-2,6-dimethylaniline according to claim 1.

8. N-(1'-methoxycarbonyl-ethyl)-N-β-chloropropionyl-2,3,6-trimethylaniline according to claim 1.

9. N-(1'-methoxycarbonyl-ethyl)-N-α-iododopropionyl-2,6-dimethylaniline according to claim 1.

10. N-(1'-methoxycarbonyl-ethyl)-N-α-chloroisobutyryl-2,6-dimethylaniline according to claim 1.

11. The D-configuration of the compounds according to claim 1.

12. A fungicidal composition which contains as active substance a fungicidally effective amount of a compound of the formula I

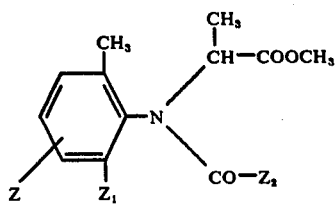

wherein
Z represents hydrogen or methyl, $Z_1$ represents methyl or ethyl, $Z_2$ represents an alkyl group of 2 to 4 carbon atoms which is substituted by a chlorine, bromine or iodine atom, together with a suitable carrier therefor.

13. A fungicidal composition according to claim 12 which contains a compound of the formula I, wherein $Z_1$ represents methyl.

14. A fungicidal composition according to claim 12 which contains a compound of the formula I, wherein Z represents hydrogen and $Z_1$ represents methyl or ethyl while $Z_2$ represents a group

in which R represents methyl or ethyl and Y represents chlorine or bromine.

15. A fungicidal composition accordng to claim 12 which contains N-(1'-methoxycarbonyl-ethyl)-N-α-chloropropionyl-2,6-dimethylaniline.

16. A fungicidal composition according to claim 12 which contains N-(1'-methoxycarbonyl-ethyl)-N-α-chlorobutyryl-2,6-dimethylaniline.

17. A fungicidal composition according to claim 12 which contains N-(1'-methoxycarbonyl-ethyl)-N-δ-chlorobutyryl-2,6-dimethylaniline.

18. A fungicidal composition according to claim 12 which contains N-(1'-methoxycarbonyl-ethyl)-N-β-chloropropionyl-2,6-dimethylaniline.

19. A fungicidal composition according to claim 12 which contains N-(1'-methoxycarbonyl-ethyl)-N-β-chloropropionyl-2,3,6-trimethylaniline.

20. A fungicidal composition according to claim 12 which contains N-(1'-methoxycarbonyl-ethyl)-N-α-iodopropionyl-2,6-dimethylaniline.

21. A fungicidal composition according to claim 12 which contains N-(1'-methoxycarbonyl-ethyl)-N-α-chloroisobutyryl-2,6-dimethylaniline.

22. A fungicidal composition according to claim 12 which contains as active substance a compound of the formula I in the D-configuration.

23. A method for combatting phytopathogenic fungi which comprises applying to the locus thereof a fungicidally effective amount of a compound of formula I according to claim 12.

* * * * *